United States Patent
Liu et al.

(10) Patent No.: US 12,012,368 B2
(45) Date of Patent: Jun. 18, 2024

(54) CAGE SILICATE AND METHOD FOR PRODUCING THE SAME

(71) Applicant: Nissan Chemical Corporation, Tokyo (JP)

(72) Inventors: Jiahao Liu, Sodegaura (JP); Takuya Fukuoka, Funabashi (JP); Hiroaki Sakaida, Toyama (JP)

(73) Assignee: NISSAN CHEMICAL CORPORATION, Tokyo (JP)

( * ) Notice: Subject to any disclaimer, the term of this patent is extended or adjusted under 35 U.S.C. 154(b) by 0 days.

(21) Appl. No.: 18/274,967

(22) PCT Filed: Feb. 15, 2023

(86) PCT No.: PCT/JP2023/005162
§ 371 (c)(1),
(2) Date: Oct. 5, 2023

(87) PCT Pub. No.: WO2023/188928
PCT Pub. Date: Oct. 5, 2023

(65) Prior Publication Data
US 2024/0051913 A1    Feb. 15, 2024

(30) Foreign Application Priority Data

Mar. 29, 2022  (JP) ................. 2022-053843

(51) Int. Cl.
C07C 211/63    (2006.01)
C07C 209/68    (2006.01)
C07C 209/84    (2006.01)

(52) U.S. Cl.
CPC .......... *C07C 211/63* (2013.01); *C07C 209/68* (2013.01); *C07C 209/84* (2013.01); *C07B 2200/13* (2013.01)

(58) Field of Classification Search
None
See application file for complete search history.

(56) References Cited

U.S. PATENT DOCUMENTS

| | | |
|---|---|---|
| 5,047,492 A | 9/1991 | Weidner et al. |
| 2008/0253953 A1 | 10/2008 | Muller et al. |
| 2011/0197762 A1 | 8/2011 | Voss et al. |
| 2012/0203019 A1 | 8/2012 | Loessel et al. |
| 2014/0053859 A1 | 2/2014 | Valia et al. |
| 2015/0224473 A1 | 8/2015 | Skinley et al. |
| 2016/0068664 A1 | 3/2016 | Suemura et al. |
| 2019/0232252 A1 | 8/2019 | Skinley et al. |
| 2020/0407230 A1 | 12/2020 | Murakami et al. |
| 2021/0061824 A1 | 3/2021 | Igarashi et al. |

FOREIGN PATENT DOCUMENTS

| | | |
|---|---|---|
| CN | 101503420 A | 8/2009 |
| CN | 101974225 A | 2/2011 |
| CN | 102171145 A | 8/2011 |
| CN | 102574873 A | 7/2012 |

(Continued)

OTHER PUBLICATIONS

English translation of the Written Opinion of the International Searching Authority for International Application No. PCT/JP2023/005162, dated Sep. 8, 2023.

(Continued)

*Primary Examiner* — Sudhakar Katakam
*Assistant Examiner* — Jennifer C Sawyer
(74) *Attorney, Agent, or Firm* — Birch, Stewart, Kolasch & Birch, LLP

(57) ABSTRACT

An object is to provide a cage silicate that can be industrially safely and simply produced by using an alkali silicate solution that does not generate alcohol as a Si raw material and using non-toxic quaternary ammonium, and a method for producing the same. The problem is solved by the following cage silicate:

A cage silicate consisting of anion component 1 represented by following formula (1), anion component 2 which is a mineral acid ion, cation component 1 represented by following formula (2), and cation component 2 which is an alkali ion, in which, to the mole number in terms of $SiO_2$, a ratio of the mole number of water, ($H_2O/SiO_2$), is 0.7 to 30, a ratio of the mole number of alkali ions, (alkali ions/$SiO_2$), is $1.0 \times 10^{-7}$ to $1.0 \times 10^{-2}$, and a ratio of the mole number of the mineral acid ions, (mineral acid ions/$SiO_2$), is $1.0 \times 10^{-7}$ to $1.0 \times 10^{-3}$.

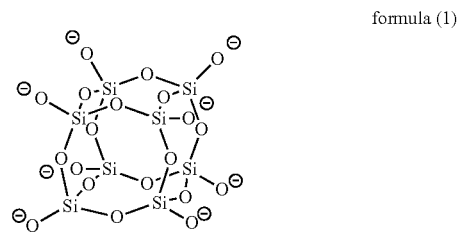

formula (1)

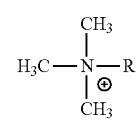

formula (2)

In formula (2), R represents an alkyl group having 2 to 20 carbon atoms.

20 Claims, No Drawings

(56) References Cited

FOREIGN PATENT DOCUMENTS

| | | |
|---|---|---|
| CN | 105263860 A | 1/2016 |
| CN | 105960281 A | 9/2016 |
| CN | 110520430 A | 11/2019 |
| CN | 111788154 A | 10/2020 |
| EP | 1 937 594 A2 | 7/2008 |
| EP | 2 151 466 A1 | 2/2010 |
| EP | 4 276 067 A1 | 11/2023 |
| JP | 2-178291 A | 7/1990 |
| JP | 2000-334881 A | 12/2000 |
| JP | 2004-51904 A | 2/2004 |
| JP | 2005-231929 A | 9/2005 |
| JP | 2008-24894 A | 2/2008 |
| JP | 2009-269820 A | 11/2009 |
| JP | 2013-40066 A | 2/2013 |
| JP | 2017-512132 A | 5/2017 |
| TW | 201414503 A | 4/2014 |
| WO | WO 2014/188934 A1 | 11/2014 |
| WO | WO 2018/193732 A1 | 10/2018 |

OTHER PUBLICATIONS

Abe et al., "Synthesis of alkoxysiloxanes and their application to materials", J. Jpn. Soc. Colour Mater., 80 (11), pp. 458-461, (2007).

Hasegawa et al., "The Effect of Tetramethylammonium Ions on the Distribution of Silicate Species in the Methanolic Solutions", Journal of Molecular Liquids, 34 (1987), pp. 307-315.

International Search Report for PCT/JP2023/005162 (PCT/ISA/210) dated Apr. 25, 2023.

Written Opinion of the International Searching Authority for PCT/JP2023/005162 (PCT/ISA/237) dated Apr. 25, 2023.

Taiwanese Office Action and Search Report for Taiwanese Application No. 112107485, dated Dec. 19, 2023, with an English translation.

Office Action issued Apr. 4, 2024, in Chinese Patent Application No. 202380009821.9.

Extended European Search Report for European Application No. 23744033.4, dated Mar. 5, 2024.

Harrison, "Silicate cages: precursors to new materials," Journal of Organometallic Chemistry, vol. 542, 1997, pp. 141-183.

CAGE SILICATE AND METHOD FOR PRODUCING THE SAME

TECHNICAL FIELD

The present invention relates to a cage silicate and a method for producing the same. More specifically, the present invention relates to a novel production method capable of producing a cage silicate more safely and/or more simply as compared with the related art, and a novel cage silicate obtained by the method for producing the cage silicate.

BACKGROUND ART

Cage silicates are known as raw materials for cage oligosilsesquioxane. Here, cage oligosilsesquioxane is attracting attention because it has a regular structure composed of a nanometer-scale siloxane backbone. In addition, due to its characteristic structure, it is expected to be used as a polymer material or a building block from multibranched polymers such as network polymers and dendrimers. Furthermore, since various organic groups can be introduced into a substituent bonded to Si, high affinity with an organic component can be expected, and it is also expected to be used as a filler for improving mechanical, thermal, and optical functions of a polymer material. Therefore, a method for producing a cage silicate has also been attracting attention. Various disclosures have been made on a cage silicate and a method for producing a cage oligosilsesquioxane using the same.

For example, Non-Patent Literature 1 discloses a method for obtaining a silicate having various structures including a cage by reacting a methanol solution of tetraethoxysilane with a methanol solution of tetramethylammonium hydroxide.

For example, Non-Patent Literature 2 discloses a method of hydrolyzing and polycondensing a trifunctional or tetrafunctional silane and a method of synthesizing a cage silsesquioxane by reacting a polysilsesquioxane having an incomplete structure generated by trifunctional or tetrafunctional silane hydrolysis polycondensation with trichlorosilane. Furthermore, it is disclosed that tetraethoxysilane is hydrolyzed in the presence of tetramethylammonium hydroxide to obtain a cage silicate with tetramethylammonium hydroxide.

For example, Patent Literature 1 discloses a method in which an aqueous tetramethylammonium hydroxide solution is added to precipitated silicic acid, the mixture is mixed at 25° C. for 16 hours and at 50° C. for 8 hours, and the tetramethylammonium silicate obtained by crystallization is reacted with 1,3-divinyl-1,1,3,3-tetramethyldisiloxane and concentrated hydrochloric acid in isopropanol to obtain octa(vinyldimethylsiloxy)octasilsesquioxane.

For example, Patent Literature 2 discloses that a mixture consisting of tetraethoxysilane and methanol is mixed, (2-hydroxyethyl)trimethylammonium hydroxide is added dropwise, and the mixture is reacted at 25 to 30° C. for 28 hours and further at 54° C. for 12 hours to obtain octapoly (tetramethylammonium)silicate as a cage silicate. In addition, Patent Literature 2 discloses that an organic/inorganic microporous silicon material can be obtained using this cage silicate.

CITATION LIST

Non-Patent Literature

NON-PATENT LITERATURE 1: ISAO HASEGAWA, SUMIO SAKKA et al, "THE EFFECT OF TETRAMETHYLAMMONIUM IONS ON THE DISTRIBUTION OF SILICATE SPECIES" Journal of Molecular Liquids, 1987, vol. 34, p 307-315

NON-PATENT LITERATURE 2: Yoshimoto Abe, Takahiro Gunji, "Synthesis of Alkoxysiloxane and its Application to Materials" J. Jpn. Soc. Colour Mater., 2007, vol. 80 (11), p. 458-461

Patent Literature

PATENT LITERATURE 1: JP H2-178291 A
PATENT LITERATURE 2: CN 101974225 A

SUMMARY OF INVENTION

Technical Problem

However, since silicon alkoxides such as tetraethoxysilane used in these production methods generate a large amount of alcohol by hydrolysis, there has been an industrial problem that dedicated facilities and wastewater treatment are required. In addition, when precipitated silicic acid that does not generate alcohol is used as a Si raw material, since the precipitated silicic acid contains a large amount of alkali ions and mineral acid ions, there has been a problem in handling that it takes time to wash the obtained cage silicic acid. Furthermore, since tetramethylammonium hydroxide used as a structure directing agent is classified as a toxic substance in the Poisonous and Deleterious Substances Control Act, it has been necessary to consider a working environment and the like.

The present invention has been made in view of the above circumstances, and an object of the present invention is to provide a cage silicate that can be industrially safely and simply produced by using an aqueous alkali silicate solution that does not generate alcohol as a Si raw material and using non-toxic quaternary ammonium, and a method for producing the same.

Solution to Problem

As a result of intensive studies to solve the above problems, the present inventors have found that a cage silicate can be obtained more safely and/or more simply by mixing a specific active silicic acid with quaternary ammonium and crystallizing the cage silicate from the mixed solution, and have achieved the present invention.

That is, although not limited to the following, the present invention and various aspects are the following [1] to [13].

[1]

A cage silicate consisting of anion component 1 represented by following formula (1), anion component 2 which is a mineral acid ion, cation component 1 represented by following formula (2), and cation component 2 which is an alkali ion, wherein a ratio of the mole number of water to the mole number in terms of $SiO_2$, ($H_2O/SiO_2$), is 0.7 to 30, a ratio of the mole number of alkali ions to the mole number in terms of $SiO_2$, (alkali ions/$SiO_2$), is $1.0 \times 10^{-7}$ to $1.0 \times 10^{-2}$, and a ratio of the mole number of the mineral acid ions to the mole number in terms of $SiO_2$, (mineral acid ions/$SiO_2$), is $1.0 \times 10^{-7}$ to $1.0 \times 10^{-3}$:

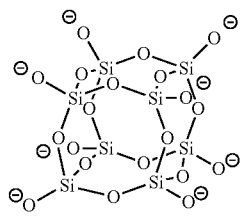

formula (1)

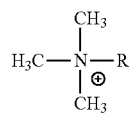

formula (2)

in formula (2), R represents an alkyl group having 2 to 20 carbon atoms.

[2]

The cage silicate according to [1], wherein the anion component represented by formula (1) is an anion component derived from an aqueous solution of anhydrous alkali silicate.

[3]

A method for producing the cage silicate according to [1], comprising following steps (a) to (c):
step (a) of removing cations of an aqueous alkali silicate solution obtained by dissolving anhydrous alkali silicate to obtain active silicic acid;
step (b) of mixing the active silicic acid obtained in step (a) with quaternary ammonium in an aqueous medium; and
step (c) of crystallizing the cage silicate from the mixed solution obtained in step (b).

[4]

The method for producing the cage silicate according to [3], wherein the quaternary ammonium is represented by following formula (3).

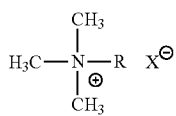

formula (3)

in formula (3), R represents an alkyl group having 2 to 20 carbon atoms, and X represents a hydroxy ion, a carbonate ion, or a halide ion.

[5]

The method for producing the cage silicate according to [3] or [4], wherein step (b) is a step of mixing the active silicic acid obtained in step (a) and the quaternary ammonium in an aqueous medium such that a ratio of the mole number of the quaternary ammonium to the mole number of the active silicic acid in terms of $SiO_2$, (quaternary ammonium/$SiO_2$), is 0.7 to 1.5.

[6]

The method for producing the cage silicate according to any one of [3] to [5], wherein a concentration of the mixed solution in terms of $SiO_2$, which is obtained in step (b), is 0.01% by mass to 10% by mass.

[7]

The method for producing the cage silicate according to any one of [3] to [6], wherein step (b) includes stirring the mixed liquid of the active silicic acid obtained in step (a) and quaternary ammonium at 10° C. to 80° C. for 30 minutes to 30 hours.

[8]

The method for producing the cage silicate according to any one of [3] to [7], wherein step (c) includes concentrating the mixed solution obtained in step (b) before crystallization.

[9]

The method for producing the cage silicate according to [8], wherein a mass concentration of the concentrated mixed solution in terms of $SiO_2$ is 1% by mass to 30% by mass.

[10]

The method for producing the cage silicate according to any one of [3] to [8], wherein step (c) includes holding the aqueous medium at a temperature lower than the temperature in step (b) and at a temperature at which the aqueous medium does not freeze.

[11]

The method for producing the cage silicate according to any one of [3] to [10], wherein
in the cage silicate obtained in step (c),
the ratio of the mole number in terms of quaternary ammonium to the mole number in terms of $SiO_2$, (quaternary ammonium/$SiO_2$), is 0.7 to 1.5, and
the ratio of the mole number of water to the mole number in terms of $SiO_2$, ($H_2O/SiO_2$), is 0.7 to 30.

[12]

The method for producing the cage silicate according to any one of [3] to [11], further including step (d) of washing the cage silicate obtained in step (c).

[13]

The method for producing the cage silicate according to [12], wherein step (d) is a step of washing the cage silicate by bringing the cage silicate obtained in step (c) into contact with a solvent, and a mass of a residue of the cage silicate after washing is 90% to 99% with respect to the cage silicate before washing.

Advantageous Effects of Invention

In the production method of the present invention, active silicic acid as Si raw materials that do not generate alcohol and quaternary ammonium having no toxicity are used, and accordingly, a cage silicate can be industrially safely and simply produced. Furthermore, in one aspect, high yields can be achieved with short production times.

DESCRIPTION OF EMBODIMENTS

A cage silicate compound of the present invention is a cage silicate consisting of anion component 1 represented by following formula (1), anion component 2 which is a mineral acid ion, cation component 1 represented by following formula (2), and cation component 2 which is an alkali ion, in which a ratio of the mole number of water to the mole number in terms of $SiO_2$, ($H_2O/SiO_2$), is 0.7 to 30, a ratio of the mole number of alkali ions to the mole number in terms of $SiO_2$, (alkali ions/$SiO_2$), is $1.0 \times 10^{-7}$ to $1.5 \times 10^{-2}$, and a ratio of the mole number of the mineral acid ions to the mole number in terms of $SiO_2$, (mineral acid ions/$SiO_2$), is $1.0 \times 10^{-7}$ to $1.0 \times 10^{-3}$.

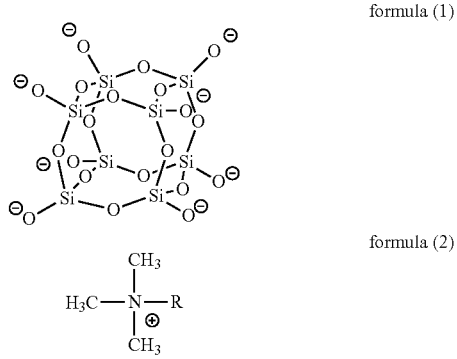

formula (1)

formula (2)

in formula (2), R represents an alkyl group having 2 to 20 carbon atoms.

The anion component 1 represented by formula (1) is a cage silicate ion having a siloxane (Si—O—Si) bond as a basic backbone.

In one aspect, the anion component 1 represented by formula (1) is an anion component derived from an aqueous solution of an anhydrous alkali silicate. The aqueous solution of the anhydrous alkali silicate can be obtained by dissolving a solid of the anhydrous alkali silicate (also referred to as cullet) in water. Examples of the anhydrous alkali silicate include anhydrous sodium silicate, anhydrous potassium silicate, and anhydrous lithium silicate. Preferably, the anhydrous alkali silicate is anhydrous sodium silicate.

The anion component 2 is a mineral acid ion. The mineral acid ion is a component derived from the anhydrous alkali silicate. Examples of the mineral acid ion include a sulfate ion, a hydrochloride ion, and a nitrate ion.

In the mineral acid ions contained in the cage silicate of the present invention, the ratio of the mole number of mineral acid ions to the mole number of the cage silicate in terms of $SiO_2$, (mineral acid ions/$SiO_2$), is $1.0 \times 10^{-7}$ to $1.0 \times 10^{-3}$. The mineral acid ions can be quantified by ion chromatography.

The mineral acid ion is a component derived from the anhydrous alkali silicate, and a ratio of the mole number of the mineral acid ion to the mole number of the cage silicate in terms of $SiO_2$, (mineral acid ion/$SiO_2$), is $1.0 \times 10^{-7}$ or more. In addition, from the viewpoint of the purity of the cage silicate of the present invention, the ratio of the mole number of the mineral acid ions to the mole number of the cage silicate in terms of $SiO_2$, (mineral acid ions/$SiO_2$), is $1.0 \times 10^{-3}$ or less. In order to adjust the amount of the mineral acid ions, the crystals of the cage silicate of the present invention may be washed. By setting the ratio of the mole number of the mineral acid ions to the mole number of the cage silicate in terms of $SiO_2$, (mineral acid ions/$SiO_2$), to $1.0 \times 10^{-3}$ or less, deterioration of performance can be prevented when the cage silicate is used as a raw material of a polymer material.

The mineral acid ions contained in the cage silicate can be expected to act as a catalyst in substituting the functional group of the cage silicate with the silane compound.

The cation component 1 represented by formula (2) is a quaternary ammonium ion.

Examples of the quaternary ammonium ion include ethyltrimethylammonium ion, propyltrimethylammonium ion, butyltrimethylammonium ion, pentyltrimethylammonium ion, hexyltrimethylammonium ion, heptyltrimethylammonium ion, octyltrimethylammonium ion, nonyltrimethylammonium ion, decyltrimethylammonium ion, undecyltrimethylammonium ion, dodecyltrimethylammonium ion, tridecyltrimethylammonium ion, tetradecyltrimethylammonium ion, pentadecyltrimethylammonium ion, hexadecyltrimethylammonium ion (cetyltrimethylammonium ion), heptadecyltrimethylammonium ion, octadecyltrimethylammonium ion, nonyldecyltrimethylammonium ion, and icosyltrimethylammonium ion. Preferably, the quaternary ammonium ion is an ethyltrimethylammonium ion, a propyltrimethylammonium ion, a butyltrimethylammonium ion, a pentyltrimethylammonium ion, a hexyltrimethylammonium ion, a heptyltrimethylammonium ion, an octyltrimethylammonium ion, or a nonyltrimethylammonium ion.

In the quaternary ammonium ions contained in the cage silicate of the present invention, the ratio of the mole number of the quaternary ammonium ions to the mole number of the cage silicate in terms of $SiO_2$, (quaternary ammonium/$SiO_2$), is 0.7 to 1.5. The amount of the quaternary ammonium ions contained in the cage silicate can be determined by measuring the amount of nitrogen using an element analyzer and converting the measured amount of nitrogen into the amount of the quaternary ammonium ions.

The cation component 2 is an alkali ion. The alkali ion is a component derived from the anhydrous alkali silicate, and examples of the alkali ion include a sodium ion, a potassium ion, and a lithium ion. Preferably, the alkali ion is a sodium ion.

In the alkali ions contained in the cage silicate of the present invention, a ratio of the mole number of the alkali ions to the mole number of the cage silicate in terms of $SiO_2$, (alkali ions/$SiO_2$), is $1.0 \times 10^{-7}$ to $1.0 \times 10^{-2}$. The alkali ions can be quantified by an atomic absorption spectrophotometer SpectrAA (manufactured by Agilent Technologies, Inc.).

The alkali ion is a component derived from the anhydrous alkali silicate, and a ratio of the mole number of the alkali ion to the mole number of the cage silicate in terms of $SiO_2$, (alkali ion/$SiO_2$), is $1.0 \times 10^{-7}$ or more. In addition, from the viewpoint of the purity of the cage silicate of the present invention, the ratio of the mole number of alkali ions to the mole number of the cage silicate in terms of $SiO_2$, (alkali ions/$SiO_2$), is $1.0 \times 10^{-2}$ or less. Preferably, the ratio of the mole number of alkali ions to the mole number of the cage silicate in terms of $SiO_2$, (alkali ions/$SiO_2$), is $5.0 \times 10^{-3}$ or less. In order to adjust the amount of the alkali ion, the crystal of the cage silicate of the present invention may be washed. When the ratio of the mole number of alkali ions to the mole number of the cage silicate in terms of $SiO_2$, (alkali ions/$SiO_2$), is $1.0 \times 10^{-2}$ or less, deterioration of performance can be prevented when the cage silicate is used as a raw material of a polymer material.

It is believed that a trace amount of the alkali ions contained in the cage silicate protects the silanol group at the apex of the cage silicate backbone. Therefore, when the cage silicate of the present invention is further modified with a substituent such as a different silane compound, a difference in reactivity occurs between a part where the silanol group is protected by the alkali ion and a part where the silanol group is protected by the quaternary ammonium ion, and it can be expected that the amount of modification by the silane compound is controlled.

Furthermore, a trace amount of the alkali ions contained in the cage silicate can be expected to act as a catalyst in substituting the functional group of the cage silicate with the silane compound.

The present invention relates to a cage silicate. The obtained compound can be identified as a cage by solid $^{29}$Si-NMR measurement or solution $^{29}$Si-NMR measurement. Specifically, the structure can be identified by evaluating the bonding state of Si by a cross polarization magic angle spinning (CP-MAS) method in solid $^{29}$Si-NMR measurement. In addition, the structure can be identified by evaluating the bonding state of Si by JNM-ECZ500 R/S1 (manufactured by JEOL Ltd.) in solution $^{29}$Si-NMR measurement.

The Si atom constituting the cage silicate has a Q3 structure bonded to one OH group and three O atoms as shown in following formula (4). In solid $^{29}$Si-NMR measurement by the CP-MAS method, a peak indicating the Q3 structure appears in the vicinity of −92 ppm to −100 ppm. Therefore, when all the measured peaks are derived from the Q3 structure, it can be identified that the product has a cage structure. In addition, by the solution $^{29}$Si-NMR measurement, a peak indicating the Q3 structure also appears in the vicinity of −92 ppm to −100 ppm. Therefore, when all the measured peaks are derived from the Q3 structure, it can be identified that the product has a cage structure.

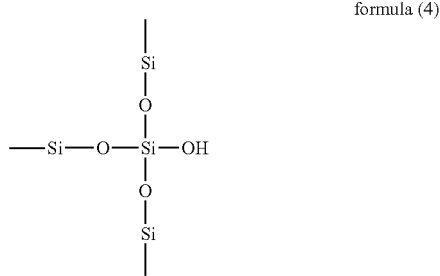

formula (4)

The cage silicate of the present invention contains water. The water is derived from adsorbed water and/or hydrated water. The amount of water contained in the cage silicate of the present invention is represented by the ratio of the mole number of water to the mole number in terms of $SiO_2$, ($H_2O/SiO_2$). The ratio of the mole number of water to the mole number in terms of $SiO_2$, ($H_2O/SiO_2$), is 0.7 to 30. The ratio of the mole number of water to the mole number of the cage silicate in terms of $SiO_2$, ($H_2O/SiO_2$), can be calculated from the mass of water contained in the cage silicate. The mass of water can be calculated by quantifying the amount of quaternary ammonium, the amount of silicon dioxide, the amount of alkali ions, and the amount of mineral acid ions contained in the obtained cage silicate, and subtracting the respective masses from the mass of the cage silicate. The amount of quaternary ammonium can be determined by measuring the amount of nitrogen using an element analyzer and converting the measured amount of nitrogen into the amount of quaternary ammonium. The amount of silicon dioxide can be determined by a firing method. The amount of alkali ions can be quantified by an atomic absorption spectrophotometer. The amount of the mineral acid ions can be calculated by summing the amounts of each type of ions measured by ion chromatography.

The ratio of the mole number of water to the mole number in terms of $SiO_2$, ($H_2O/SiO_2$), is 0.7 or more. The ratio of the mole number of water to the mole number in terms of $SiO_2$, ($H_2O/SiO_2$), may be preferably 1.0 or more, and more preferably 1.5 or more, depending on the application of the cage silicate. The ratio of the mole number of water to the mole number in terms of $SiO_2$, ($H_2O/SiO_2$), is 30 or less. The ratio of the mole number of water to the mole number in terms of $SiO_2$, ($H_2O/SiO_2$), may be preferably 20 or less, and more preferably 10 or less, depending on the application of the cage silicate. Depending on the amount of water contained in the cage silicate of the present invention, the compound generated by various reactions using the cage silicate of the present invention may be changed. The method for adjusting the amount of water is not particularly limited, for example, the method includes removing water from the cage silicate by holding the obtained cage silicate at 20° C. to 80° C. under vacuum or reduced pressure of $5.0\times10^{-2}$ Pa to 100 Pa for approximately 30 minutes to 10 hours.

A method for producing the cage silicate of the present invention is a method for producing a cage silicate including following steps (a) to (c):

step (a) of removing cations of an aqueous alkali silicate solution obtained by dissolving anhydrous alkali silicate to obtain active silicic acid;

step (b) of mixing the active silicic acid obtained in step (a) with quaternary ammonium in an aqueous medium; and step (c) of crystallizing the cage silicate from the mixed solution obtained in step (b).

<Step (a)>

Step (a) is a step of removing cations of an aqueous alkali silicate solution obtained by dissolving anhydrous alkali silicate to obtain active silicic acid.

Examples of the anhydrous alkali silicate include anhydrous sodium silicate, anhydrous potassium silicate, and anhydrous lithium silicate.

The aqueous alkali silicate solution is obtained by dissolving anhydrous alkali silicate in water, and is an aqueous solution containing a silicate ion or a silicate ion monomer and an alkali metal ion. Specific examples of the aqueous alkali silicate solution include an aqueous sodium silicate solution in which anhydrous sodium silicate is dissolved, an aqueous potassium silicate solution in which anhydrous potassium silicate is dissolved, and an aqueous lithium silicate solution in which anhydrous lithium silicate is dissolved. The anhydrous alkali silicate such as anhydrous sodium silicate can be obtained by a known method. For example, the anhydrous sodium silicate is obtained by melting silicon dioxide and sodium carbonate or sodium hydroxide at a high temperature, and when the obtained anhydrous sodium silicate is subjected to an autoclave treatment together with water, a highly viscous aqueous sodium silicate solution can be obtained. The aqueous sodium silicate solution is also referred to as water glass.

As described above, the aqueous alkali silicate solution obtained by dissolving the anhydrous alkali silicate does not produce alcohol in step (b) to be described later as compared with the case where tetraethoxysilane is used as a Si source. Therefore, there is no need for a dedicated facility and a discharge treatment, and the cage silicate can be relatively easily produced.

As the aqueous alkali silicate solution, a commercially available product can be used. For example, the aqueous alkali silicate solution is available from Tokuyama Corporation, AICHIKEISO Co., Ltd., Oriental Silicas Corporation, and the like.

In general, an aqueous alkali silicate solution is commercially available at a $SiO_2$ concentration of 30 to 50% by mass. In the production method of the present invention, the commercially available aqueous alkali silicate solution may be used as it is, or used as an aqueous solution having a $SiO_2$ concentration of 0.5% by mass to 10% by mass by diluting the commercially available aqueous alkali silicate solution with water. Also, the mole ratio of $M_2O$ (M represents sodium, potassium, lithium, or the like) to $SiO_2$ in the commercially available aqueous alkali silicate solution, ($M_2O/SiO_2$), is not particularly limited.

The active silicic acid is obtained by removing cations contained in the aqueous alkali silicate solution. A known method can be used as a method for removing cations. For example, sodium ions can be removed by bringing an aqueous sodium silicate solution into contact with an H-form cation exchange resin. The contact can be performed by a batch method or a column method, and industrially, a method of filling an ion exchange tower with a cation exchange resin and passing an aqueous alkali silicate solution therethrough can be used. The liquid passage rate is 1 to 30 at a space velocity (L/hr), and the liquid passage can be performed at a temperature of 10 to 80° C. Examples of the cation exchange resin include a sulfonic acid type H-form strongly acidic cation exchange resin and a carboxylic acid type H-form weakly acidic cation exchange resin. Preferably, the sulfonic acid type strongly acidic cation exchange resin can be used by shaping to H-form.

Examples of the sulfonic acid type strongly acidic cation exchange resin include trade name AmberLite (registered trademark) IR-120B manufactured by Organo Corporation.

In addition, the $SiO_2$ concentration of the aqueous alkali silicate solution during liquid passage can be 0.5% by mass to 15% by mass, and preferably 1% by mass to 10% by mass.

For the purpose of reducing impurities of the obtained active silicic acid, a step of removing anions may be performed before or after removing cations of the aqueous alkali silicate solution. In addition, a washing step using an ultrafiltration device may be performed before or after removing cations of the aqueous alkali silicate solution. Alternatively, a step of removing anions such as metal ions using a chelating agent or a chelating resin may be performed before or after removing cations of the aqueous alkali silicate solution.

<Step (b)>

Step (b) is a step of mixing the active silicic acid obtained in step (a) with quaternary ammonium in an aqueous medium. More specifically, step (b) may include charging the active silicic acid and the quaternary ammonium into an aqueous medium to form a mixed liquid, and stirring the mixed liquid for a certain period of time.

As the quaternary ammonium, a compound represented by following formula (3) can be used.

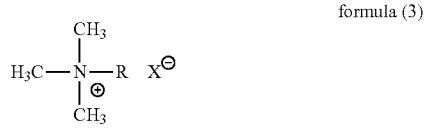

formula (3)

In formula (3), R represents an alkyl group having 2 to 20 carbon atoms, and X represents a hydroxy ion, a carbonate ion, or a halide ion.

Examples of the quaternary ammonium represented by formula (3) include hydroxides such as ethyltrimethylammonium hydroxide, propyltrimethylammonium hydroxide, butyltrimethylammonium hydroxide, pentyltrimethylammonium hydroxide, hexyltrimethylammonium hydroxide, heptyltrimethylammonium hydroxide, octyltrimethylammonium hydroxide, nonyltrimethylammonium hydroxide, decyltrimethylammonium hydroxide, undecyltrimethylammonium hydroxide, dodecyltrimethylammonium hydroxide, tridecyltrimethylammonium hydroxide, tetradecyltrimethylammonium hydroxide, pentadecyltrimethylammonium hydroxide, hexadecyltrimethylammonium hydroxide (cetyltrimethylammonium hydroxide), heptadecyltrimethylammonium hydroxide, octadecyltrimethylammonium hydroxide, nonyltrimethylammonium hydroxide, and icosyltrimethylammonium hydroxide.

Further, examples of the quaternary ammonium include carbonates such as ethyltrimethylammonium carbonate, propyltrimethylammonium carbonate, butyltrimethylammonium carbonate, pentyltrimethylammonium carbonate, hexyltrimethylammonium carbonate, heptyltrimethylammonium carbonate, octyltrimethylammonium carbonate, nonyltrimethylammonium carbonate, decyltrimethylammonium carbonate, undecyltrimethylammonium carbonate, dodecyltrimethylammonium carbonate, tridecyltrimethylammonium carbonate, tetradecyltrimethylammonium carbonate, pentadecyltrimethylammonium carbonate, hexadecyltrimethylammonium carbonate (cetyltrimethylammonium carbonate), heptadecyltrimethylammonium carbonate, octadecyltrimethylammonium carbonate, nonyldecyltrimethylammonium carbonate, and icosyltrimethylammonium carbonate.

In addition, examples of the quaternary ammonium include chlorides such as ethyltrimethylammonium chloride, propyltrimethylammonium chloride, butyltrimethylammonium chloride, pentyltrimethylammonium chloride, hexyltrimethylammonium chloride, heptyltrimethylammonium chloride, octyltrimethylammonium chloride, nonyltrimethylammonium chloride, decyltrimethylammonium chloride, undecyltrimethylammonium chloride, dodecyltrimethylammonium chloride, tridecyltrimethylammonium chloride, tetradecyltrimethylammonium chloride, pentadecyltrimethylammonium chloride, hexadecyltrimethylammonium chloride (cetyltrimethylammonium chloride), heptadecyltrimethylammonium chloride, octadecyltrimethylammonium chloride, nonyldecyltrimethylammonium chloride, and icosyltrimethylammonium chloride.

Further, examples of the quaternary ammonium include bromides such as ethyltrimethylammonium bromide, propyltrimethylammonium bromide, butyltrimethylammonium bromide, pentyltrimethylammonium bromide, hexyltrimethylammonium bromide, heptyltrimethylammonium bromide, octyltrimethylammonium bromide, nonyltrimethylammonium bromide, decyltrimethylammonium bromide, undecyltrimethylammonium bromide, dodecyltrimethylammonium bromide, tridecyltrimethylammonium bromide, tetradecyltrimethylammonium bromide, pentadecyltrimethylammonium bromide, hexadecyltrimethylammonium bromide (cetyltrimethylammonium bromide), heptadecyltrimethylammonium bromide, octadecyltrimethylammonium bromide, nonyldecyltrimethylammonium bromide, and icosyltrimethylammonium bromide.

Preferably, the quaternary ammonium may be ethyltrimethylammonium hydroxide, propyltrimethylammonium hydroxide, butyltrimethylammonium hydroxide, pentyltrimethylammonium hydroxide, hexyltrimethylammonium hydroxide, heptyltrimethylammonium hydroxide, octyltrimethylammonium hydroxide, and nonyltrimethylammonium hydroxide.

In step (b), the active silicic acid and the quaternary ammonium can be mixed such that the ratio of the mole number of the quaternary ammonium to the mole number of the active silicic acid in terms of $SiO_2$, (quaternary ammonium/$SiO_2$), is 0.7 to 1.5. Preferably, the active silicic acid and the quaternary ammonium can be mixed such that the ratio of the mole number of the quaternary ammonium to the mole number of the active silicic acid in terms of $SiO_2$, (quaternary ammonium/$SiO_2$), is 1.0 to 1.5. By mixing the active silicic acid and the quaternary ammonium such that the ratio of the mole number of the quaternary ammonium to the mole number of the active silicic acid in terms of $SiO_2$, (quaternary ammonium/$SiO_2$), is 0.7 to 1.5, the cage silicate can be obtained without causing excess or deficiency.

In addition, in step (b), the concentration of the mixed solution in terms of $SiO_2$ may be by mass to 10% by mass. Preferably, the concentration of the mixed solution in terms of $SiO_2$ can be 1.0% by mass to 10% by mass. The concentration of the mixed solution in terms of $SiO_2$ can be calculated based on the $SiO_2$ concentration of the aqueous alkali silicate solution obtained in step (a). By setting the concentration of the mixed solution in terms of $SiO_2$ to by mass to 10% by mass, the cage silicate can be efficiently crystallized in step (c) described later.

Step (b) may include stirring the mixed liquid of the active silicic acid obtained in step (a) and the quaternary ammonium at 10° C. to 80° C. for 30 minutes to 30 hours. Preferably, the temperature in step (b) may be 15° C. to 40° C. For the stirring time, a mixed liquid of the active silicic acid and the quaternary ammonium may be sufficiently stirred.

The stirring time is preferably 10 hours or less, and more preferably 5 hours or less. By setting the stirring time to 30 hours or less, the cage silicate can be efficiently obtained. When the concentration of the mixed solution in terms of $SiO_2$ is increased by concentrating the mixed liquid before step (c) described later, the stirring time can be shortened.

<Step (c)>

Step (c) is a step of crystallizing the cage silicate from the mixed solution obtained in step (b). Specifically, the mixed solution obtained in step (b) is cooled to crystallize the cage silicate. In step (c), the temperature dependence of the solubility of the cage silicate in the aqueous solvent can be utilized to crystallize and separate the cage silicate from the solution by cooling.

In addition, step (c) may include concentrating the mixed solution obtained in step (b) before crystallizing the cage silicate. The concentration can be performed by a known method. For example, the concentration of the mixed solution in terms of $SiO_2$ can be increased while removing the solvent under reduced pressure using an evaporator. The concentration of the mixed liquid after concentration in terms of $SiO_2$ can be 1% by mass to 30% by mass. Preferably, the concentration of the mixed liquid after concentration in terms of $SiO_2$ can be 5% by mass to 20% by mass. By setting the concentration in terms of $SiO_2$ to 1% by mass to 30% by mass, the $SiO_2$ yield of the cage silicate can be increased. Also, when the concentration of the mixed solution in terms of $SiO_2$ is increased by concentration in step (c), the stirring time in step (b) may be shortened.

Furthermore, in step (c), in order to promote the crystallization of the cage silicate, a seed crystal such as an existing cage silicate may be added to the mixed liquid obtained in step (b). The seed crystal may be added at the time of cooling the mixed liquid obtained in step (b) or at the time of the concentration step.

Step (c) may include holding the mixed liquid at a temperature lower than the temperature of step (b) and at a temperature at which the aqueous medium does not freeze. The temperature may be, for example, 0° C. to 10° C. when water is used as the medium. Preferably, the temperature may be between 0° C. and 5° C. When the temperature is 0° C. or higher, freezing of the aqueous solvent can be prevented. When the temperature is 10° C. or lower, crystallization of the cage silicate can be promoted. The holding time may be from 30 minutes to 24 hours. Preferably, the holding time may be between 3 hours and 24 hours. When the holding time is 30 minutes or more, the cage silicate can be sufficiently crystallized. When the holding time is 24 hours or less, the production time can be shortened, and the cage silicate can be efficiently obtained.

After the cage silicate is crystallized, the cage silicate can be separated and recovered by filtering the mixed solution containing the cage silicate. The filtration can be performed by a known method. Examples of the filtration method include allowing the mixed solution to pass through a quantitative filter paper having a holding particle size of 1 μm to separate and recover the cage silicate.

<Step (d)>

The method for producing the cage silicate of the present invention may further include step (d). Step (d) is a step of washing the cage silicate obtained in step (c). Specifically, after the cage silicate obtained in step (c) is separated and recovered by filtration or the like, the cage silicate can be washed by bringing the cage silicate into contact with a solvent. The mass of the residue of the cage silicate after washing (after solvent contact) can be 90% to 99% with respect to the cage silicate obtained in step (c) before washing (before solvent contact). By performing step (d), alkali ions and mineral acid ions contained in the cage silicate can be reduced. As the solvent used for washing in step (d), acetone, methanol, ethanol, IPA, or the like can be used. By selecting such the solvents, it is possible to efficiently reduce alkali ions and mineral acid ions while suppressing dissolution of the cage silicate in the solvent. As a method for bringing the cage silicate into contact with the solvent, for example, the recovered cage silicate may be added in the solvent and stirred/mixed. In addition, the cage silicic acid obtained in step (c) may be separated and recovered with filter paper or the like, and then the solvent may be added dropwise a plurality of times to the cage silicate recovered on the filter paper.

In the cage silicate obtained by the production method of the present invention, the ratio of the mole number in terms of quaternary ammonium to the mole number in terms of $SiO_2$, (quaternary ammonium/$SiO_2$), is 0.7 to 1.5, and the ratio of the mole number of water to the mole number in terms of $SiO_2$, ($H_2O/SiO_2$), is 0.7 to 30.

Also, in the method for producing the cage silicate of the present invention, water may be removed after step (c) or step (d) in order to adjust the amount of water of the obtained cage silicate.

The removal of water from the cage silicate can be performed at a temperature of approximately 20° C. to 80° C. under vacuum or under reduced pressure. For example, water can be removed by holding at a predetermined temperature in a vacuum dryer having a degree of vacuum ($5.0 \times 10^{-2}$ Pa to 500 Pa). In particular, in order to efficiently remove water, it is preferable to perform at $5.0 \times 10^{-2}$ Pa to 100 Pa. The holding temperature may be approximately to 80° C., and preferably approximately 40° C. to 70° C. Holding may be performed at a constant temperature, or may be performed by changing the temperature in two stages or three stages. The holding time may be 30 minutes to 10 hours, and preferably 1 hour to 6 hours. Since water can be appropriately removed by drying for 30 minutes or more, a holding time of minutes or more is preferable. The holding time can exceed 10 hours, but when the amount of water is constant and the holding time is more than that, since removal effect becomes lower, the holding time of 10 hours or less is efficient.

The cage silicate obtained by the production method of the present invention may further contain alkali ions. In the alkali ions contained in the cage silicate, a ratio of the mole number of the alkali ions to the mole number in terms of $SiO_2$, (alkali ions/$SiO_2$), is $1.0\times10^{-7}$ to $1.0\times10^{-2}$. In addition, the cage silicate may further contain a mineral acid ion. In the mineral acid ions contained in the cage silicate, the ratio of the mole number of the mineral acid ions to the mole number in terms of $SiO_2$, (mineral acid ions/$SiO_2$), is $1.0\times10^{-7}$ to $1.0\times10^{-3}$.

EXAMPLES

Hereinafter, the present invention will be described with reference to Examples, but the present invention is not limited to these Examples.

The structure of the cage silicate was identified by the following method.

(1) Quantification of $SiO_2$ Concentration of Active Silicic Acid and Cage Silicate The active silicic acid and the cage silicate were fired at 1000° C., and the $SiO_2$ concentration was calculated from the obtained fired residues.

(2) Identification of Structure of Cage Silicate (CP-MAS Method)

The obtained silicate powder was measured by a CP-MAS method using a solid $^{29}$Si-NMR apparatus AVANCE3500 (manufactured by Bruker Corporation). Identification of the cage silicate was performed by confirming that a signal derived from Si of the Q3 structure appears only in the vicinity of −92 ppm to −100 ppm.

(3) Identification of Structure of Cage Silicate

The obtained silicate powder was dissolved in deuterium-substituted methanol and measured with a solution $^{29}$Si-NMR apparatus JNM-ECZ500R/S1 (manufactured by JEOL Ltd.). Identification of the cage silicate was performed by confirming that a signal derived from Si of the Q3 structure appears only in the vicinity of −92 ppm to −100 ppm.

(4) Quantification of Alkali Ion Amount of Cage Silicate

The obtained cage silicate powder was measured by an atomic absorption spectrophotometer SpectrAA (manufactured by Agilent Technologies, Inc.). The measured amount of sodium ions was taken as the amount of alkali ions.

(5) Quantification of Quaternary Ammonium Amount of Cage Silicate

The amount of nitrogen was measured by measuring the obtained cage silicate powder with an element analyzer Perkin Elmer 2400 Series2 CHNS/O Analyzer (manufactured by Perkin Elmer Japan Co., Ltd.). The measured amount of nitrogen was converted to the amount of quaternary ammonium.

(6) Calculation of Mineral Acid Ion Amount of Cage Silicate

The amounts of hydrochloride ions, nitrate ions, and sulfate ions were measured by measuring the obtained cage silicate powder by ion chromatography using an anion analyzer Dionex ICS-2100 (manufactured by Themo SCIENTIFIC). The total of the measured amounts of hydrochloride ions, nitrate ions, and sulfate ions was taken as the mineral acid ion amount.

(7) Calculation of Amount of Water of Cage Silicate

The amount of water of the cage silicate was calculated by subtracting the respective values from the mass of the cage silicate based on the amount of quaternary ammonium, the amount of silicon dioxide, the amount of alkali ions, and the amount of mineral acid ions, which were quantified in (1), (4), (5), and (6). In addition, the ratio of the mole number of water to the mole number of the cage silicate in terms of $SiO_2$, ($H_2O/SiO_2$), was calculated based on the amount of water.

(8) Method for Measuring Yield of $SiO_2$

The ratio of the amount of $SiO_2$ contained in the cage silicate quantified in (1) to the mass of $SiO_2$ contained in the aqueous alkali silicate solution used as a raw material was defined as a yield.

Example 1

450.0 g of water glass No. 4 (manufactured by Nippon Chemical Industrial Co., Ltd., $SiO_2$:$Na_2O$:$H_2O$ mole ratio: 3.9:1:39.0, $SiO_2$ concentration: 23.4% by mass, $Na_2O$ concentration: 6.3% by mass) was diluted with pure water to obtain 3.6% of water glass aqueous solution. The water glass aqueous solution was subjected to cation exchange with a cation exchange resin (Amberlite 120B manufactured by Organo Corporation) to obtain 3004.9 g of active silicic acid. 1764.7 g (1.0 mol) of the obtained active silicic acid ($SiO_2$ concentration: 3.4%) and 525.0 g (1.0 mol) of an aqueous solution of ethyltrimethylammonium hydroxide (manufactured by SACHEM Japan Gogo Kaisha, concentration: 20% by weight) were added to a 3 L recovery flask, and the mixture was stirred at room temperature for 24 hours with a propeller blade. The mixed solution was concentrated under reduced pressure to a mass concentration of 11.7% by mass in terms of $SiO_2$ using an evaporator, and then allowed to stand at 5° C. for 12 hours to precipitate crystals. The mixed solution containing the crystals was subjected to suction filtration using a quantitative filter paper 5B (manufactured by ADVANTEC) and solid-liquid separation, thereby recovering 225.9 g of the cage silicate ($SiO_2$ concentration: 16.2% by weight, $SiO_2$:$ETMA^+$:$H_2O$ molar ratio: 1.0:0.9:12.8). In addition, it was confirmed by a CP-MS method using a solid $^{29}$Si-NMR apparatus that the product was a cage silicate.

Example 2

88.2 g (0.05 mol) of the active silicic acid ($SiO_2$ concentration: 3.4%) obtained in the same procedure as in Example 1 and 150.8 g (0.05 mol) of an aqueous solution of cetyltrimethylammonium hydroxide (manufactured by Tokyo Chemical Industry Co., Ltd., concentration: 10% by weight) were added to a 3 L recovery flask and stirred at room temperature by a propeller blade for 24 hours. The mixture was allowed to stand at 5° C. for 12 hours to precipitate crystals. The mixed solution containing the crystals was subjected to suction filtration using the quantitative filter paper 5B and solid-liquid separation, thereby recovering 14.2 g of the cage silicate ($SiO_2$ concentration: 9.1% by weight, $SiO_2$:$CTMA^+$:$H_2O$ mole ratio: 1.0:0.6:4.4). In addition, it was confirmed that the product was a cage silicate using a solution $^{29}$Si-NMR apparatus.

Example 3

1764.7 g (1.0 mol) of the active silicic acid ($SiO_2$ concentration: 3.4%) obtained in the same procedure as in Example 1 and 525.0 g (1.0 mol) of an aqueous solution of ethyltrimethylammonium hydroxide (manufactured by SACHEM Japan Godo Kaisha, concentration: 20% by weight) were added to a 3 L recovery flask, and the mixture was stirred at room temperature by a propeller blade for 4 hours. The mixed solution was concentrated under reduced pressure to a mass concentration of 15.2% by mass in terms of $SiO_2$ using an evaporator, and then allowed to stand at 5° C. for 12 hours to precipitate crystals. The mixed solution containing the crystals was subjected to solid-liquid separation by suction filtration using the quantitative filter paper 5B to recover 297.4 g of the cage silicate ($SiO_2$ concentration: 16.2% by weight, $SiO_2$:$ETMA^+$:$H_2O$ mole ratio: 1.0:0.9:12.8). In addition, it was confirmed by a CP-MS method using a solid $^{29}Si$-NMR apparatus that the product was a cage silicate.

Comparative Example 1

174.4 g (0.1 mol) of the active silicic acid ($SiO_2$ concentration: 3.4%) obtained in the same procedure as in Example 1 and 73.6 g (0.1 mol) of an aqueous solution of tetraethylammonium hydroxide (manufactured by FUJIFILM Wako Pure Chemical Corporation, concentration: 20% by weight) were added to a 3 L recovery flask, and the mixture was stirred at room temperature by a propeller blade for 24 hours. After stirring, the solution became cloudy and gelled. No precipitation of crystals was observed.

Comparative Example 2

34.9 g (0.02 mol) of the active silicic acid ($SiO_2$ concentration: 3.4%) obtained in the same procedure as in Example 1 and 40.7 g (0.02 mol) of an aqueous solution of tetrapropylammonium hydroxide (manufactured by Tokyo Chemical Industry Co., Ltd., concentration: 10% by weight) were added to a 3 L recovery flask and stirred at room temperature by a propeller blade for 24 hours. After stirring, the solution became cloudy and gelled. No precipitation of crystals was observed.

Comparative Example 3

348.8 g (0.2 mol) of the active silicic acid ($SiO_2$ concentration: 3.4%) obtained in the same procedure as in Example 1 and 129.74 g (0.2 mol) of an aqueous solution of tetrabutylammonium hydroxide (manufactured by Tokyo Chemical Industry Co., Ltd., concentration: 40% by weight) were added to a 3 L recovery flask and stirred at room temperature by a propeller blade for 24 hours. While the mixed solution was concentrated under reduced pressure by an evaporator, the solution became cloudy and gelled. No precipitation of crystals was observed.

Comparative Example 4

20.0 g (0.3 mol) of the precipitated silicic acid Tokusil NP (manufactured by Oriential Silicas Corporation, $SiO_2$ concentration: 99.9% by mass), 174.9 g (0.3 mol) of an aqueous solution of ethyltrimethylammonium hydroxide (manufactured by SACHEM Japan Godo Kaisha, concentration: 20% by weight), and 174.9 g of pure water were added to a 1 L recovery flask, and the mixture was stirred at room temperature by a propeller blade for 8 hours. Thereafter, the mixture was stirred by a propeller blade at 50° C. for 8 hours. 118.9 g of the mixed solution ($SiO_2$ concentration: 5.4% by mass) was concentrated under reduced pressure to a mass concentration of 11.6% by mass in terms of $SiO_2$ by an evaporator, and then allowed to stand at 5° C. for 12 hours to precipitate crystals. The mixed solution containing the crystals was subjected to suction filtration using the quantitative filter paper 5B (manufactured by ADVANTEC) and solid-liquid separation, thereby recovering 38.7 g of the obtained crystals ($SiO_2$ concentration: 13.2% by mass).

Table 1 shows the raw materials used in each of the examples, the production conditions of the cage silicate, the measurement results of the obtained cage silicate, and the yields of $SiO_2$. In addition, Table 2 shows the raw materials used in each of the comparative examples, the production conditions of the cage silicate, the measurement results of the obtained cage silicate, and the yields of $SiO_2$.

TABLE 1

|  | Example 1 | Example 2 | Example 3 |
|---|---|---|---|
| Raw materials supplied |  |  |  |
| Raw materials | Aqueous sodium silicate Active silicic acid | Aqueous sodium silicate Active silicic acid | Aqueous sodium silicate Active silicic acid |
| Quaternary ammonium | Ethyltrimethylammonium hydroxide ETMAH | Cetyltrimethylammonium hydroxide CTMAH | Ethyltrimethylammonium hydroxide ETMAH |
| Cage silicate producing conditions |  |  |  |
| Base/$SiO_2$ (mole ratio) | 1/1 | 1/1 | 1/1 |
| Concentration in terms of $SiO_2$ (% by mass) | 2.7 | 1.4 | 2.7 |
| Stirring condition in step (b) | Room temperature × 24 hours | Room temperature × 24 hours | Room temperature × 4 hours |
| Concentration after performing concentration in terms of $SiO_2$ (% by mass) | 11.7 | No concentration step | 15.2 |
| Crystallizing condition in step (c) | 5° C. × 12 hours | 5° C. × 12 hours | 5° C. × 12 hours |
| Cage silicate |  |  |  |
| Base/$SiO_2$ (mole ratio) | 0.9 | 0.6 | 0.9 |
| $H_2O$/$SiO_2$ (mole ratio) | 18.2 | 4.4 | 18.2 |

TABLE 1-continued

|  | Example 1 | Example 2 | Example 3 |
|---|---|---|---|
| Alkali ions/$SiO_2$ (mole ratio) | $2.7 \times 10^{-3}$ | $2.7 \times 10^{-3}$ | $2.7 \times 10^{-3}$ |
| Mineral acid anion/$SiO_2$ (mole ratio) | $7.5 \times 10^{-4}$ | $7.5 \times 10^{-4}$ | $7.5 \times 10^{-4}$ |
| $SiO_2$ yield (%) | 61% | 60% | 80% |

TABLE 2

|  | Comparative Example 1 | Comparative Example 2 | Comparative Example 3 | Comparative Example 4 |
|---|---|---|---|---|
| Raw materials supplied |  |  |  |  |
| Raw materials | Aqueous sodium silicate Active silicic acid | Aqueous sodium silicate Active silicic acid | Aqueous sodium silicate Active silicic acid | Precipitated silicic acid (Tokusil) |
| Quaternary ammonium | Tetraethylammonium hydroxide TEAOH | Tetrapropylammonium hydroxide TPAOH | Tetrabutylammonium hydroxide TBAOH | Ethyltrimethylammonium hydroxide ETMAH |
| Cage silicate producing conditions |  |  |  |  |
| Base/$SiO_2$ (mole ratio) | 1/1 | 1/1 | 1/1 | 1/1 |
| Concentration in terms of $SiO_2$ (% by mass) | 2.4 | 1.6 | 2.5 | 5.4 |
| Stirring condition in step (b) | Room temperature × 24 hours | Room temperature × 24 hours | Room temperature × 24 hours | Room temperature × 81 hours + 50° C. × 8 hours |
| Concentration after performing concentration in terms of $SiO_2$ (% by mass) | No concentration step | No concentration step | Become cloudy in the middle of concentration | 11.6 |
| Crystallizing condition in step (c) | Crystallization is impossible | Crystallization is impossible | Crystallization is impossible | 5° C. × 12 hours |
| Cage silicate |  |  |  |  |
| Base/$SiO_2$ (mole ratio) | Measurement is impossible | Measurement is impossible | Measurement is impossible | Not measured |
| $H_2O$/$SiO_2$ (mole ratio) | Measurement is impossible | Measurement is impossible | Measurement is impossible | Not measured |
| Alkali ions/$SiO_2$ (mole ratio) | Measurement is impossible | Measurement is impossible | Measurement is impossible | $1.4 \times 10^{-2}$ |
| Mineral acid anion/$SiO_2$ (mole ratio) | Measurement is impossible | Measurement is impossible | Measurement is impossible | $5.0 \times 10^{-3}$ |
| $SiO_2$ yield (%) | Measurement is impossible | Measurement is impossible | Measurement is impossible | Not measured |

INDUSTRIAL APPLICABILITY

The method for producing a cage silicate of the present invention has a remarkable technical effect that a cage silicate can be obtained industrially safely and simply because a quaternary ammonium which does not generate alcohol and does not have toxicity is used. In addition, the cage silicate of the present invention can be used as a raw material for various compounds such as cage oligosilsesquioxane. Therefore, the present invention has high applicability in various fields of industries such as chemical industries, daily necessities industries, cosmetic industries, and various other manufacturing industries, which utilize cage silicates or various compounds made from cage silicates.

The invention claimed is:

1. A cage silicate consisting of anion component 1 represented by following formula (1), anion component 2 which is a mineral acid ion, cation component 1 represented by following formula (2), and cation component 2 which is an alkali ion, wherein a ratio of the mole number of water to the mole number in terms of $SiO_2$, ($H_2O$/$SiO_2$), is 0.7 to 30, a ratio of the mole number of alkali ions to the mole number in terms of $SiO_2$, (alkali ions/$SiO_2$), is $1.0 \times 10^{-7}$ to $1.0 \times 10^{-2}$, and a ratio of the mole number of the mineral acid ions to the mole number in terms of $SiO_2$, (mineral acid ions/$SiO_2$), is $1.0 \times 10^{-7}$ to $1.0 \times 10^{-3}$:

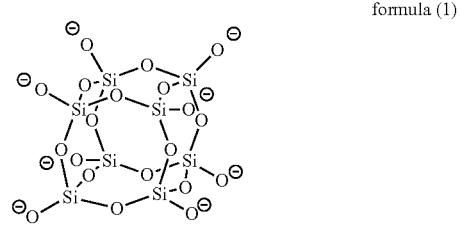

formula (1)

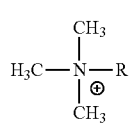

formula (2)

wherein in formula (2), R represents an alkyl group having 2 to 20 carbon atoms.

2. The cage silicate according to claim 1, wherein the anion component represented by formula (1) is an anion component derived from an aqueous solution of anhydrous alkali silicate.

3. A method for producing the cage silicate according to claim 1, comprising the following steps (a) to (c):
   step (a) of removing cations of an aqueous alkali silicate solution obtained by dissolving anhydrous alkali silicate to obtain active silicic acid;
   step (b) of mixing the active silicic acid obtained in step (a) with quaternary ammonium in an aqueous medium; and
   step (c) of crystallizing the cage silicate from the mixed solution obtained in step (b).

4. The method for producing the cage silicate according to claim 3, wherein the quaternary ammonium is represented by following formula (3):

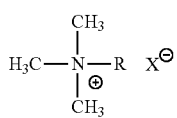

formula (3)

wherein in formula (3), R represents an alkyl group having 2 to 20 carbon atoms, and X represents a hydroxy ion, a carbonate ion, or a halide ion.

5. The method for producing the cage silicate according to claim 3, wherein step (b) is a step of mixing the active silicic acid obtained in step (a) and the quaternary ammonium in an aqueous medium such that a ratio of the mole number of the quaternary ammonium to the mole number of the active silicic acid in terms of $SiO_2$, (quaternary ammonium/$SiO_2$), is 0.7 to 1.5.

6. The method for producing the cage silicate according to claim 3, wherein a concentration of the mixed solution in terms of $SiO_2$, which is obtained in step (b), is 0.01% by mass to 10% by mass.

7. The method for producing the cage silicate according to claim 3, wherein step (b) includes stirring the mixed liquid of the active silicic acid obtained in step (a) and the quaternary ammonium at 10° C. to 80° C. for 30 minutes to 30 hours.

8. The method for producing the cage silicate according to claim 3, wherein step (c) includes concentrating the mixed solution obtained in step (b) before crystallization.

9. The method for producing the cage silicate according to claim 8, wherein a mass concentration of the concentrated mixed solution in terms of $SiO_2$ is 1% by mass to 30% by mass.

10. The method for producing the cage silicate according to claim 3, wherein step (c) includes holding the aqueous medium at a temperature lower than the temperature in step (b) and at a temperature at which the aqueous medium does not freeze.

11. The method for producing the cage silicate according to claim 3, wherein
    in the cage silicate obtained in step (c),
    the ratio of the mole number in terms of quaternary ammonium to the mole number in terms of $SiO_2$ (quaternary ammonium/$SiO_2$) is 0.7 to 1.5, and
    the ratio of the mole number of water to the mole number in terms of $SiO_2$, ($H_2O/SiO_2$), is 0.7 to 30.

12. The method for producing the cage silicate according to claim 3, further comprising step (d) of washing the cage silicate obtained in step (c).

13. The method for producing the cage silicate according to claim 12, wherein step (d) is a step of washing the cage silicate by bringing the cage silicate obtained in step (c) into contact with a solvent, and a mass of a residue of the cage silicate after washing is 90% to 99% with respect to the cage silicate before washing.

14. The method for producing the cage silicate according to claim 4, wherein step (b) is a step of mixing the active silicic acid obtained in step (a) and the quaternary ammonium in an aqueous medium such that a ratio of the mole number of the quaternary ammonium to the mole number of the active silicic acid in terms of $SiO_2$, (quaternary ammonium/$SiO_2$), is 0.7 to 1.5.

15. The method for producing the cage silicate according to claim 4, wherein a concentration of the mixed solution in terms of $SiO_2$, which is obtained in step (b), is 0.01% by mass to 10% by mass.

16. The method for producing the cage silicate according to claim 4, wherein step (b) includes stirring the mixed liquid of the active silicic acid obtained in step (a) and the quaternary ammonium at 10° C. to 80° C. for 30 minutes to 30 hours.

17. The method for producing the cage silicate according to claim 4, wherein step (c) includes concentrating the mixed solution obtained in step (b) before crystallization.

18. The method for producing the cage silicate according to claim 4, wherein step (c) includes holding the aqueous medium at a temperature lower than the temperature in step (b) and at a temperature at which the aqueous medium does not freeze.

19. The method for producing the cage silicate according to claim 4, wherein
    in the cage silicate obtained in step (c),
    the ratio of the mole number in terms of quaternary ammonium to the mole number in terms of $SiO_2$ (quaternary ammonium/$SiO_2$) is 0.7 to 1.5, and
    the ratio of the mole number of water to the mole number in terms of $SiO_2$, ($H_2O/SiO_2$), is 0.7 to 30.

20. The method for producing the cage silicate according to claim 4, further comprising step (d) of washing the cage silicate obtained in step (c).

* * * * *